US006152950A

United States Patent [19]

Shealy et al.

[11] Patent Number: 6,152,950

[45] Date of Patent: Nov. 28, 2000

[54] APPARATUS FOR THERAPEUTIC TREATMENT OF LOW BACK PAIN

[75] Inventors: C. Norman Shealy, Fairgrove, Mo.; Carlos Becerra, Atlanta, Ga.; Joseph Medeiros, Lantana, Fla.; Charity Martin, Douglasville, Ga.

[73] Assignee: Cluster Technology Corp., Tampa, Fla.

[21] Appl. No.: 09/052,665

[22] Filed: Mar. 31, 1998

[51] Int. Cl.[7] .......... A61F 5/00

[52] U.S. Cl. .......... 606/243; 606/242; 606/241

[58] Field of Search .......... 606/243, 240, 606/241, 242, 244, 245, 148, 151; 602/32, 33, 35; 5/611, 610, 617, 618, 621, 622, 624, 607; 73/862.041, 849, 828, 821; 128/845

[56] References Cited

U.S. PATENT DOCUMENTS

| | | | |
|---|---|---|---|
| 780,988 | 1/1905 | Gorham . | |
| 1,213,373 | 1/1917 | Hollowell . | |
| 2,774,349 | 12/1956 | Judovich | 606/243 |
| 2,787,262 | 4/1957 | Warner | 606/243 |
| 2,787,506 | 4/1957 | Travisano | 601/24 |
| 2,861,565 | 11/1958 | Lapierre | 606/243 |
| 2,873,457 | 2/1959 | Joy | 5/83.1 |
| 2,910,061 | 10/1959 | Rabjohn . | |
| 3,060,929 | 10/1962 | Zivi . | |
| 3,527,202 | 9/1970 | Donzelle | 600/21 |
| 3,709,217 | 1/1973 | Powers . | |
| 3,771,518 | 11/1973 | Greissing | 606/243 |
| 3,888,243 | 6/1975 | Powlan . | |
| 4,002,165 | 1/1977 | Lind . | |
| 4,236,265 | 12/1980 | Carradine . | |
| 4,432,356 | 2/1984 | Sarrell et al. . | |
| 4,579,109 | 4/1986 | Lundblad . | |
| 4,602,619 | 7/1986 | Wolf et al. . | |
| 4,627,422 | 12/1986 | Bates . | |
| 4,627,423 | 12/1986 | Kampner . | |
| 4,672,697 | 6/1987 | Schurch | 5/62 |
| 4,686,968 | 8/1987 | Scherger . | |
| 4,700,696 | 10/1987 | Schoffstall . | |
| 4,930,524 | 6/1990 | Van Zuilichem | 128/896 |
| 4,951,654 | 8/1990 | Gambale et al. . | |
| 4,991,572 | 2/1991 | Chases . | |
| 4,995,378 | 2/1991 | Dyer et al. . | |
| 5,024,214 | 6/1991 | Hayes . | |
| 5,092,322 | 3/1992 | Gantz | 602/35 |
| 5,094,228 | 3/1992 | Reinert . | |

(List continued on next page.)

FOREIGN PATENT DOCUMENTS

| | | |
|---|---|---|
| 1065270 | 5/1954 | France . |
| 2269978 | 12/1975 | France . |

OTHER PUBLICATIONS

C. Norman Shealy, MD, PhD, and Vera Borgmeyer, RN, MA, *Emerging Technologies: Preliminary Findings, Decompression, Reduction, and Stabilization of the Lumbar Spine: A Cost–Effective Treatment for Lumbosacral Pain*, American Journal of Pain Management, vol. 7, No. 2, Apr. 1997.

*Primary Examiner*—Justine R. Yu

*Attorney, Agent, or Firm*—Allen,Dyer,Doppelt,Milbrath & Gilchrist,P.A.

[57] ABSTRACT

A therapeutic traction table for the treatment of low back pain includes a bed pivotable from a vertical to a horizontal position for facilitating the placement of a person in a horizontal position on the bed. An upper body harness and underarm supports anchor the upper body of the person to the bed. A lower body harness is attached to the lower body pelvic portion of the person, and includes an inflatable air bladder for positioning within the posterior cavity of the lumbar spine formed between the lower back of the person and the bed for relaxing low back muscles during a pulling force on the spine. A traction unit includes a strap connected to the lower body harness for providing a pulling force between the upper body and the lower body. The traction unit is vertically movable from a position generally along an axis of the spine to a vertically displaced position for pulling at a pre-selected and measurable angle to the axis of the spine and isolating the pulling force to a preselected portion of the spine during a programmable back treatment protocol.

35 Claims, 13 Drawing Sheets

U.S. PATENT DOCUMENTS 5,176,707 1/1993 Phillips .
5,217,488 6/1993 Wu .
5,306,231 4/1994 Cullum et al. .
5,308,359 5/1994 Lossing .
5,312,323 5/1994 McAninch ................................ 602/32
5,387,186 2/1995 Edland .
5,401,236 3/1995 Summerville ............................. 602/33
5,655,238 8/1997 Stickley et al. ............................. 5/618
5,667,529 9/1997 Butner .
5,681,272 10/1997 Lee .

APPARATUS FOR THERAPEUTIC TREATMENT OF LOW BACK PAIN

FIELD OF INVENTION

The present invention generally relates to the therapeutic treatment of the back and more particularly to treatment of low back pain.

BACKGROUND OF THE INVENTION

Pain in the lumbosacral spine is the most common of all pain complaint. It causes loss of work and is the single most common cause of disability in persons under 45 years of age. Such is described in various well-known references directed to acute low back problems and in particular articles addressing pain management. Traction-like methods are well known for pain relief. Although pelvic traction has been used to treat patients with low back pain for hundreds of years, most neurosurgeons and orthopedists have not been enthusiastic about it secondary to concerns over inconsistent results and cumbersome equipment. Simple traction has been known to be highly effective. However, few pain clinics ever include traction as part of their approach. Various authors have reported varying techniques which widen disc spaces, decompress the discs, unload the vertebrate, reduce disc protrusion, reduce muscle spasm, separate vertebrate, and lengthen and stabilize the spine.

As addressed by C. Norman Shealy et al in the Fifth Edition of *Pain Management, a Practical Guide for Clinicians,* St. Lucie Press 1998, C. Norman Shealy et al addresses concepts in back pain management that include decompression, reduction and stabilization. Four broad categories of low back pain syndrome are identified as acute muscular low back paid which is usually self-limiting, acute low back pain involving sciatic radiation, chronic low back pain which has recurring symptoms modified by therapy, and neoplastic low back pain syndrome which is recurring, but eventually becoming progressive, constant, and intractable. Each type of low back pain syndrome has common features which vary with the intensity of the syndrome. Typically they will include regional pain, impairment and mechanical dysfunction exacerbated by activities of daily living, and mood and behavioral changes. It is agreed generally that all need to be addressed for overall successful outcome.

Mechanical traction is the technique of applying a distracting force to produce either a realignment of a structural abnormality or to relief abnormal pressure on nociceptive receptor systems. When successful, the patient clinically reports symptomatic improvement of well-being and objective clinical verification of improved range of motion, reduction of muscle spasm, improvement in regional tenderness, and improved neuropathic signs. Various therapeutic traction devices are known in the art. By way of example, U.S. Pat. No. 4,995,378 to Dyer et al describes a therapeutic table for providing traction in a prone position to a patient's lumbar region. A pelvic belt is rigidly anchored to the lower body section of the table. The patient lies prone face down on the table top. With arms above the head, the patient holds onto hand grips. The lower body section of the table to which the pelvic belt is attached is then separated from an upper body section of the table for applying traction to the lumbar region of the spine. Such anchoring of the upper body by use of the arms and partial frictional force of the body on the bed can be painful for weak or elderly patients.

U.S. Pat. No. 4,432,356 to Sarrell et al discloses a therapeutic traction table for statically or intermittently applying a traction force to the body of a patient. As is typically found for therapeutic traction tables, a straight traction force along the axis of the spine is applied to the patient while lying in a horizontal position on the bed of the table. Further, various harnessing devices have been disclosed for securing the patient to a traction device such as described in U.S. Pat. No. 5,217,488 to Wu for a motor operated traction device and U.S. Pat. No. 5,094,228 to Reinert for an apparatus for treatment of the back.

Although various therapeutic traction devices are disclosed, none provide for directing distraction forces to preselected areas of the spine and, in particular, to the lumbar spine. There is a need in the art to provide a therapeutic traction device that is easy for a clinician to use, facilitates placing of the patient for treatment, and can direct distraction forces to specific vertebrate in the lumbar spine to produce decompression or unloading due to distraction in positioning of intervertebral discs and facet joints.

SUMMARY OF THE INVENTION

In view of the foregoing background, it is therefore an object of the present invention to deliver a controllable pulling force to the lumbar vertebrae, specifically L5–S1 to L1 for producing a decompression reduction and stabilization of the lumbar spine for the treatment of low back pain. It is further an object of the present invention to isolate the pulling force to the lumbar spine by anchoring the upper body while applying a pulling force to the lower body at preselected angles to the axis of the spine.

These and other objects, features, and advantages of the invention, are provided by a therapeutic apparatus useful in the treatment of low back pain. The apparatus comprises a bed having a lower bed portion slidable from an opposing upper bed portion for movement therefrom while supporting a person in a reclined position on the bed, upper body anchoring means for anchoring the upper body of the person to the bed, a lower body harness for attaching to the lower body pelvic portion of the person, the lower body harness having an inflatable air bladder for positioning within the posterior cavity of the lumbar spine formed between the lower back of the person and the bed when the person is in a supine position on the bed, the air bladder enabling the local paraspinal muscles of the person to relax during a pulling force on the spine of the person, and traction means operable with the lower body harness for providing a pulling force between the upper body and the lower body, the traction means vertically movable from a position generally along an axis of the spine to a vertically displaced position for pulling at an angle to the axis of the spine and isolating the pulling force to a preselected portion of the spine.

The apparatus further comprises pivotally tilting means adapted for pivoting the bed between a horizontal position and a vertical position for facilitating positioning of the person onto the bed. A platform is attached to the bed for receiving the person when the bed is in the vertical position. An elongated hand rail extends along a side of the bed.

In a preferred embodiment of the present invention, the upper body anchoring means comprises a pair of arm supports carried by the bed and positionable at multiple locations for conforming to the size of the person being anchored to the bed. The anchoring means further comprises an upper body harness in combination with the pair of arm supports. The upper body harness has a rear strap for anchoring to the bed and a girdle for extending around the upper body of the person. The girdle has adjustable fastening means for fitting along the chest of the person.

Further, a preferred embodiment includes the traction means provided by a frame having an upwardly extending support, a track carried by the upwardly extending support, and a traction unit slidably carried by the track. The traction unit includes a strap extending therefrom and attached to the lower body harness for providing the pulling force to the harness created by the traction unit. Angle determining means indicates the angle to the axis through which the pulling force is exerted.

A method aspect of the invention includes providing the bed for supporting a person in a reclined position thereon, the bed being rotatable from a horizontal position to a vertical position and having a platform for receiving the person when the bed is in the vertical position. The method further includes the steps of tilting the bed to a vertical position, attaching upper body anchoring means to the person for anchoring the upper body of the person to the upper bed portion, attaching a lower body harness to the lower body pelvic portion of the person, the lower body harness having an inflatable air bladder for positioning within the posterior cavity of the lumbar spine formed between the lower back of the person and the bed when the person is in a supine position on the bed, the air bladder enabling the local paraspinal muscles of the person to relax during a pulling force on the spine of the person, and positioning the person on the platform while facing away from the bed, the back of the person proximate the bed, for preparing the person prior to positioning in a reclining position. Then, the bed is tilted for placing the bed and person in the horizontal position. The upper body harness is then anchored to the upper bed portion. Traction means is provided for placing the persons spine in traction. The method further includes the steps of attaching the traction means to the lower body harness for providing a pulling force between the upper body and the lower body of the person, positioning the traction means vertically above an axis of the spine for providing for pulling the lower body at an angle to the axis of the spine, selecting a pulling angle for isolating the pulling force to a preselected portion of the spine, and pulling at the angle for a preselected sequence of pulling forces.

BRIEF DESCRIPTION OF DRAWINGS

A preferred embodiment of the invention and alternate embodiments are described by way of example with reference to the accompanying drawings in which.

DETAILED DESCRIPTION OF PREFERRED EMBODIMENTS

The present invention will now be described more fully hereinafter with reference to the accompanying drawings, in which preferred embodiments of the invention are shown. This invention may, however, be embodied in many different forms and should not be construed as limited by the embodiments set forth herein. Rather, these embodiments are provided so that this disclosure will be thorough and complete, and will fully convey the scope of the invention to those skilled in the art. Like numbers refer to like elements throughout.

Figure 1:
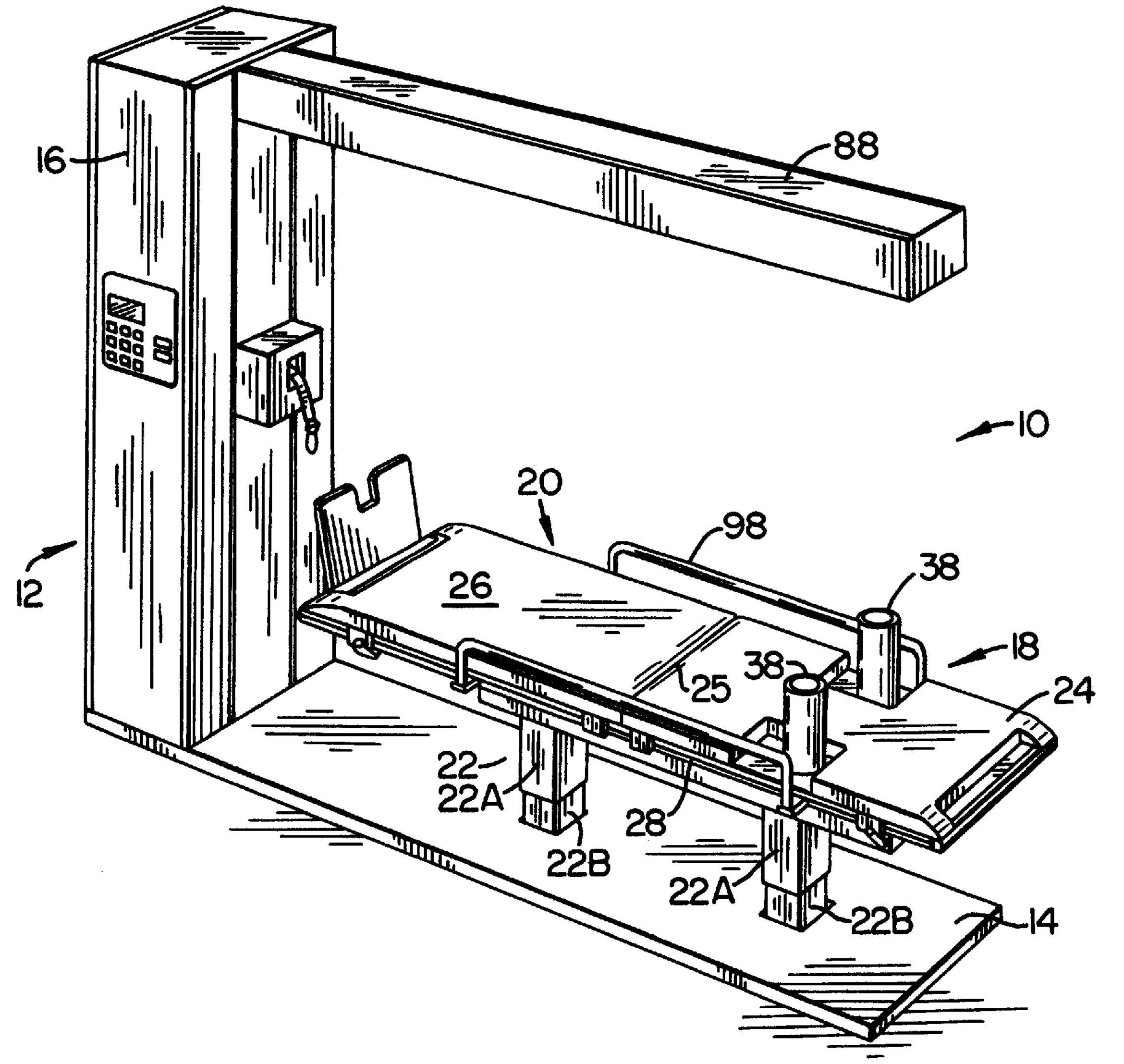
FIG. 1 is a top right, front perspective view of a preferred embodiment in accordance with the present invention.
Figure 2:
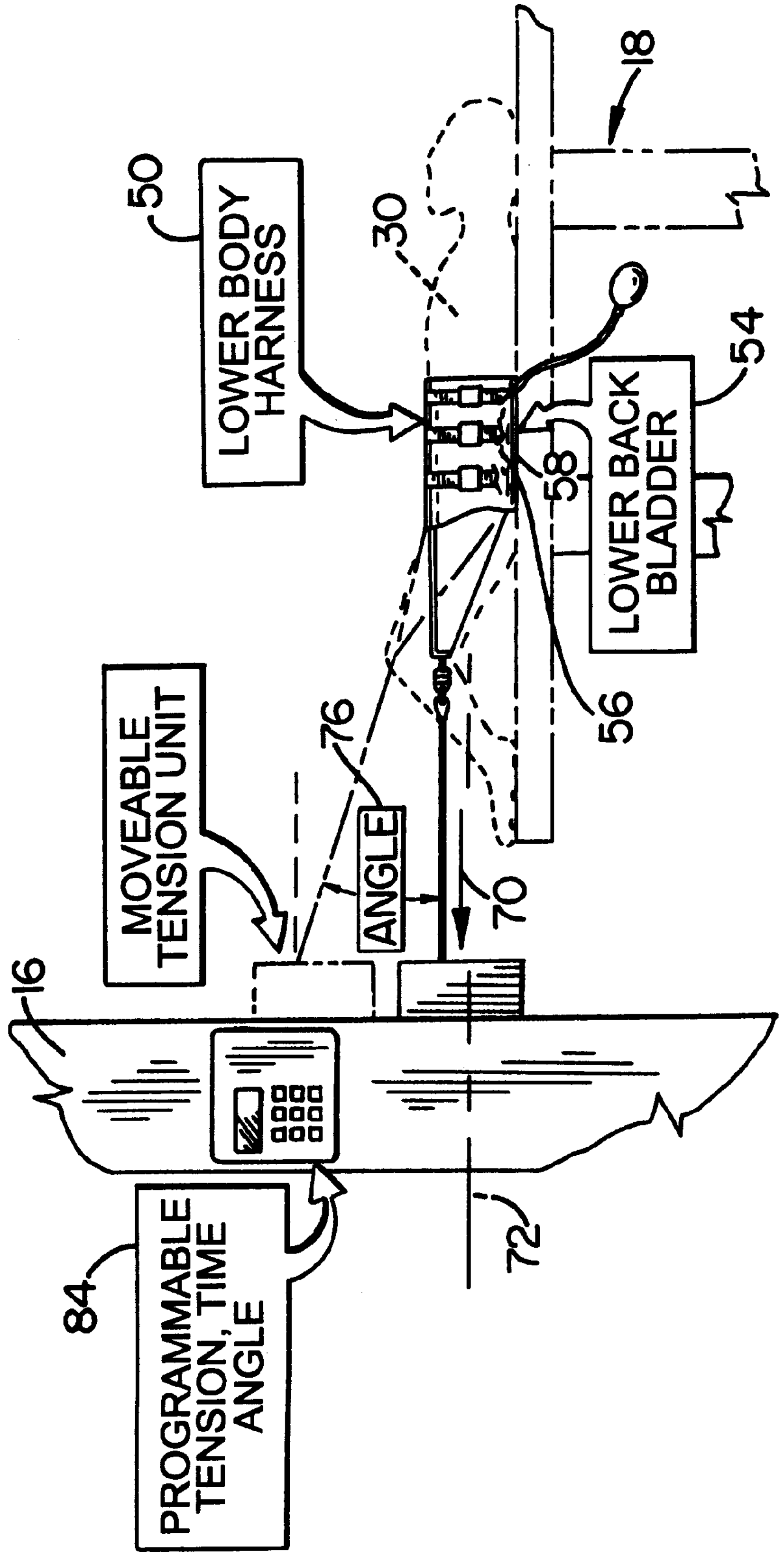
FIG. 2 is a partial diagramical elevation view of FIG. 1 illustrating elements of the present invention.
Figure 3:
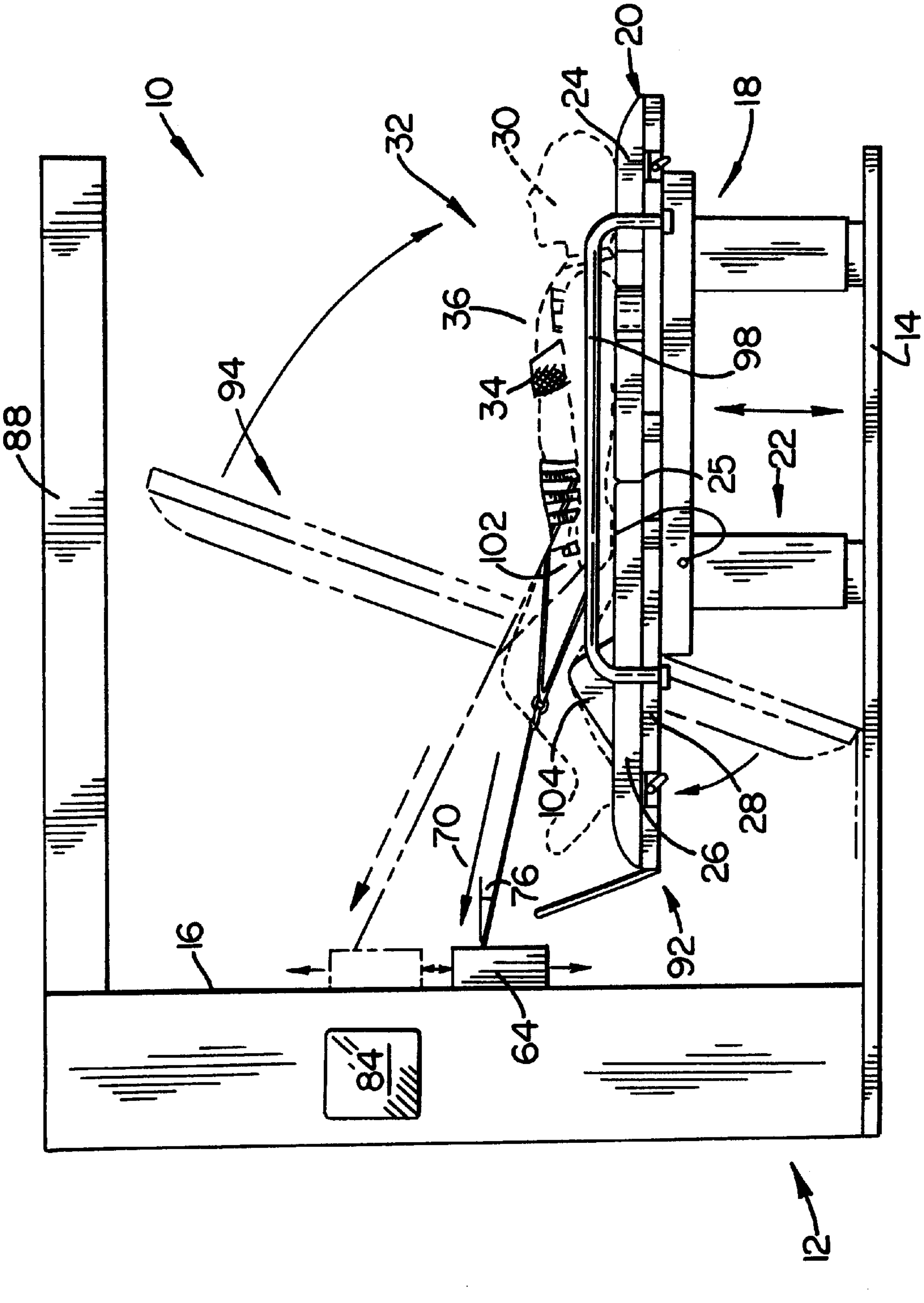
FIG. 3 is a front elevation view of FIG. 1 illustrating the person positioned on the bed in a horizontal position.

A preferred embodiment of the present invention is initially described with reference to FIG. 1, in which a therapeutic apparatus 10 useful in the treatment of low back pain comprises a frame 12 having a base 14 and a support 16 extending upwardly from the base. A table 18 includes a bed 20 and a pedestal 22 supporting the bed above the base. The pedestal 22 includes pedestal sections 22A, 22B telescopically operable for raising and lowering the bed 20, useful for placing the bed at a height convenient for the clinician operating the apparatus 10. The bed 20 has an upper bed portion 24 and an opposing lower bed portion 26 slidable therefrom along slide rails 28 for movement therefrom while supporting a person 30 in a reclined position 32 on the bed as illustrated with reference to FIGS. 2 and 3.

Figure 4:
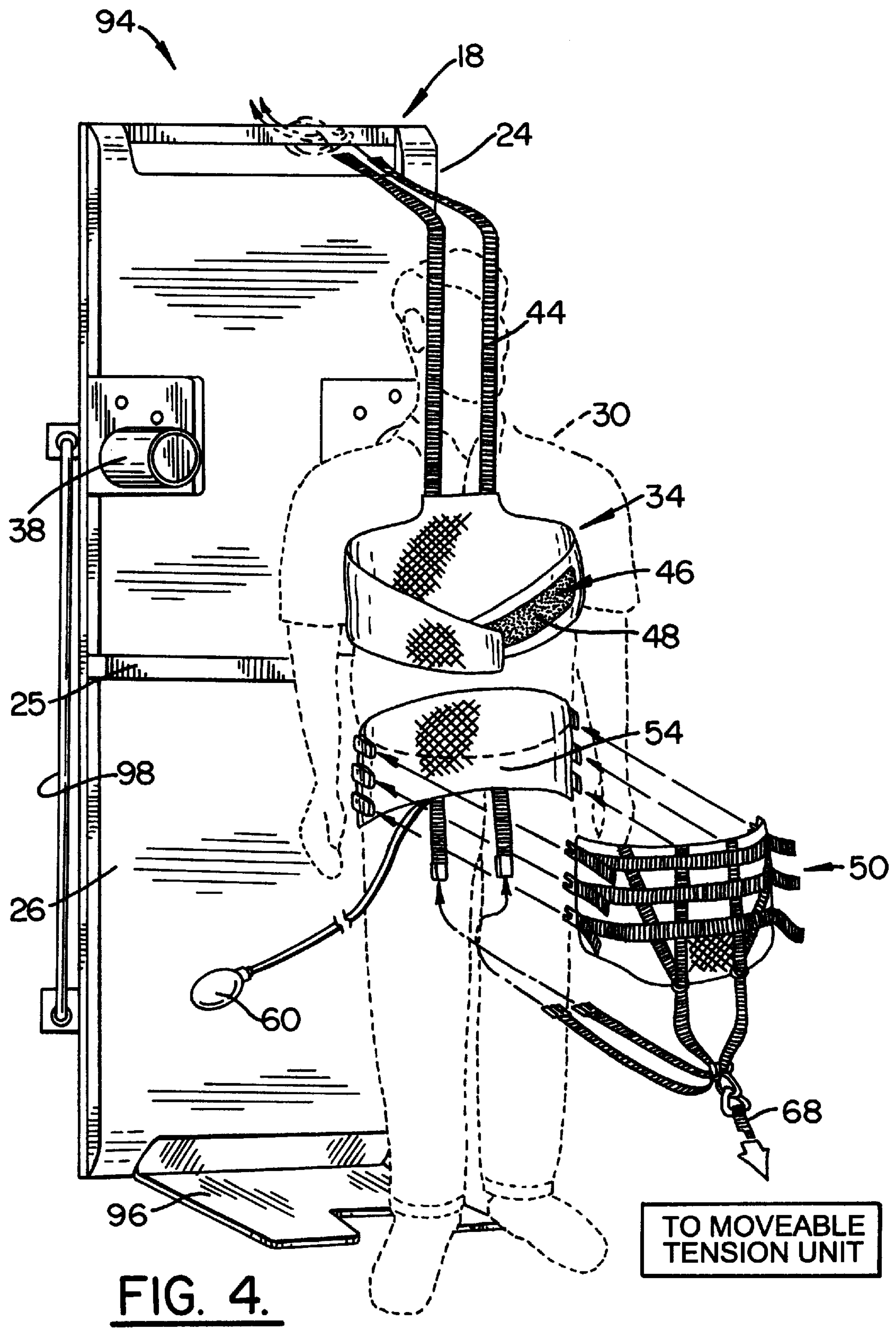
FIG. 4 is a partial exploded view elevation view of FIG. 1 illustrating a vertical position for facilitating placing a person onto a bed.
Figure 5:
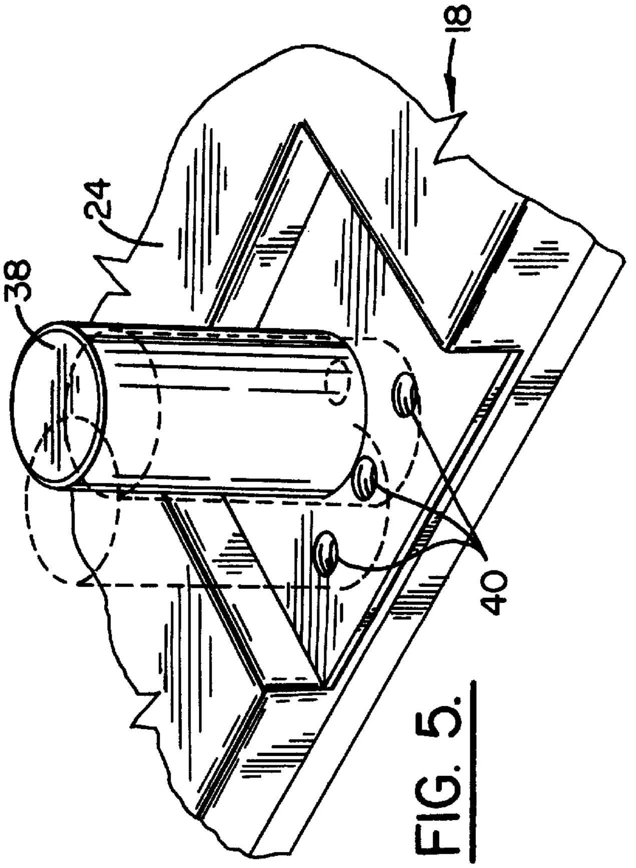
FIG. 5 is a partial top perspective view of arm supports positioned on the bed.

Upper body anchoring support 34 is provided for anchoring the upper body 36 of the person to the upper bed portion 24, as illustrated with reference again to FIG. 3 and to FIG. 4. In a preferred embodiment, the upper body anchoring support 34 comprises a pair of arm supports 38 carried by the table 18 for positioning at selected multiple locations 40 for conforming to the size of the person 30 being anchored to the upper bed portion 24, as illustrated with reference again to FIG. 4 and to FIG. 5. The arm supports 38 include a cushion around a center post for positioning the post within holes at the multiple arm support locations 40 for comfortably fitting within the underarms of the person 30. In a preferred embodiment, secure and comfortable anchoring of the upper body 36 further includes an upper body harness 42 in combination with the pair of arm supports 38. As illustrated again with reference to FIG. 4, the upper body harness 42 includes a rear strap 44 for anchoring to the table 18 above the head of the person 30 and a girdle 46 for extending around the upper body 36 of the person 30. The girdle 46 includes the use of the trademarked VELCRO to provide convenient adjustable fastening and fitting along the chest of the person 30. When positioning the person 30 for placement on the bed 20, the waist of the person is aligned proximate the gap 25 formed between the upper 24 and lower 26 bed portions. Once aligned, the upper bed portion 24 is locked in place and made secure to the table as is the upper body of the person 36. With the lower bed portion 26 slidable with respect to the upper bed portion 24, the lower body pelvic portion of the person 52 will move freely without friction between lower body pelvic portion and lower bed portion, a desirable feature when focusing distracting forces on the spine. The lower bed portion and lower body pelvic portion of the person thus move together.

Figure 7:
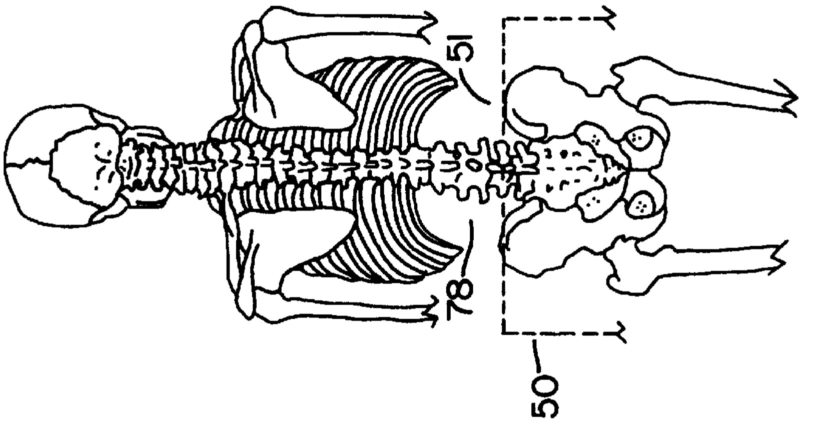
FIG. 7 is a partial rear elevation view of a human skeletal system.
Figure 6:
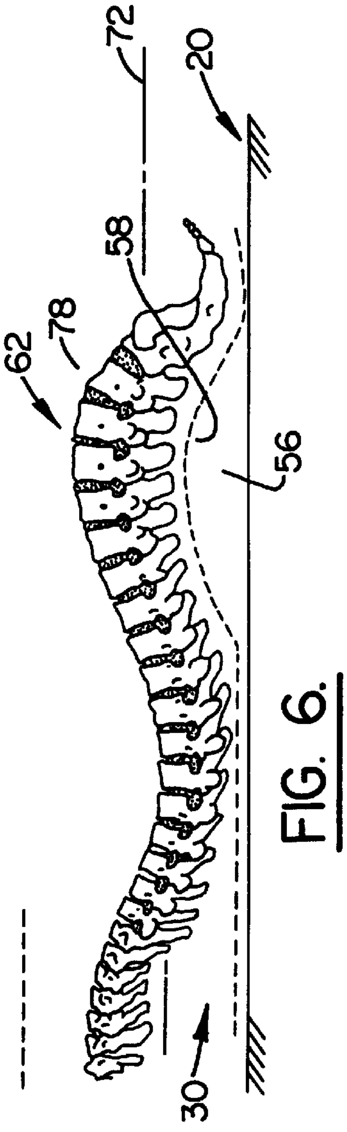
FIG. 6 is a partial side view of a human vertebrae.

As illustrated with reference again to FIGS. 2–4, a lower body harness 50 is provided for attaching to the lower body pelvic portion 52 of the person 30. The lower body harness 50 includes an inflatable air bladder 54 for positioning within the posterior cavity 56 of the lumbar spine formed between the lower back 58 of the person 30 and the bed 20 when the person is in a supine position on the bed, as illustrated with reference again to FIG. 2 and to FIG. 6. The air bladder 54 is inflatable through the use of a hand pump 60 and enables the local paraspinal muscles of the person to relax during a pulling force on the spine 62 of the person 30 for enhancing the treatment. Properly fit, the lower body harness 50 will cover the iliac crests 51 with an upper edge of the harness, as illustrated with reference to FIG. 7.

Figure 8:
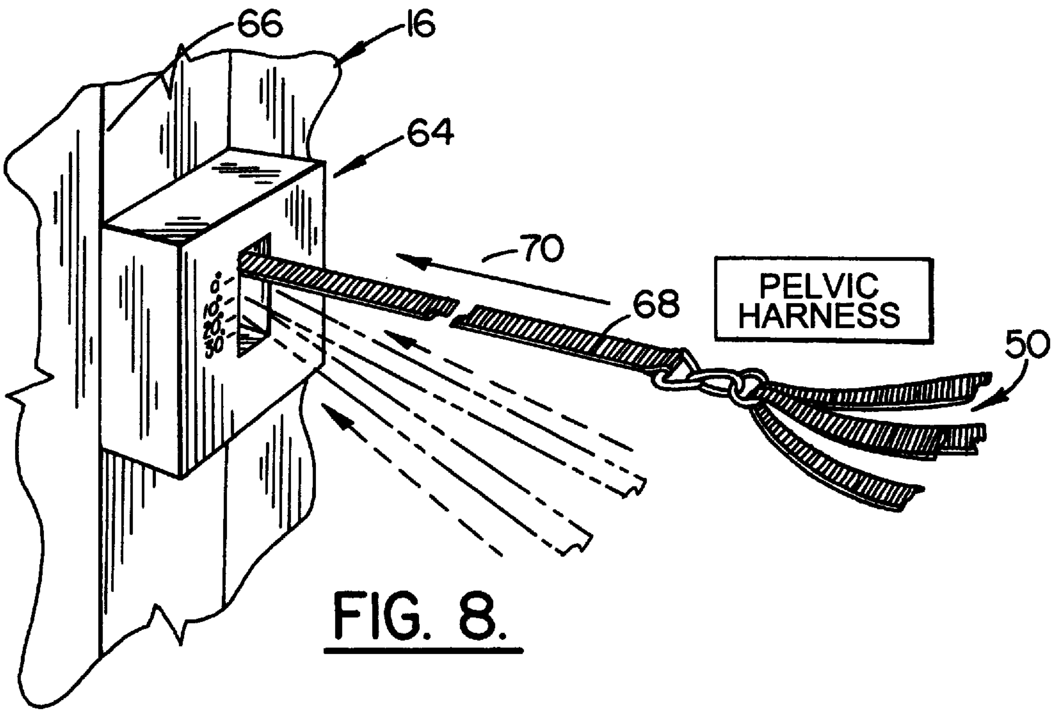
FIG. 8 is a partial perspective view of a tension unit of FIG. 1.

With reference again to FIGS. 1–3, a traction unit 64 is used for placing the person's spine in traction. The traction unit 64 is carried within a track 66 within the upwardly extending support 16 of the frame 12 and includes a strap 68 that is attached to the lower body harness 50 for providing a pulling force indicated by arrow 70 of FIGS. 2, 3 and 8 between the upper body 36 and the lower body 62 of the person 30. The traction unit 64 is vertically movable along the upwardly extending support 16 from a position generally along an axis 72 of the spine 62 (defining a zero degree angle) to a vertically displaced position 74 for pulling at an angle 76 to the axis 72 of the spine greater than zero degrees. By providing such an angle 76, the pulling force 70 is isolated to a pulling force on a preselected portion of the spine 62, in particular, to the lumbar spine 78 and the L1 through L5–S1 vertebrae.

Figure 9:
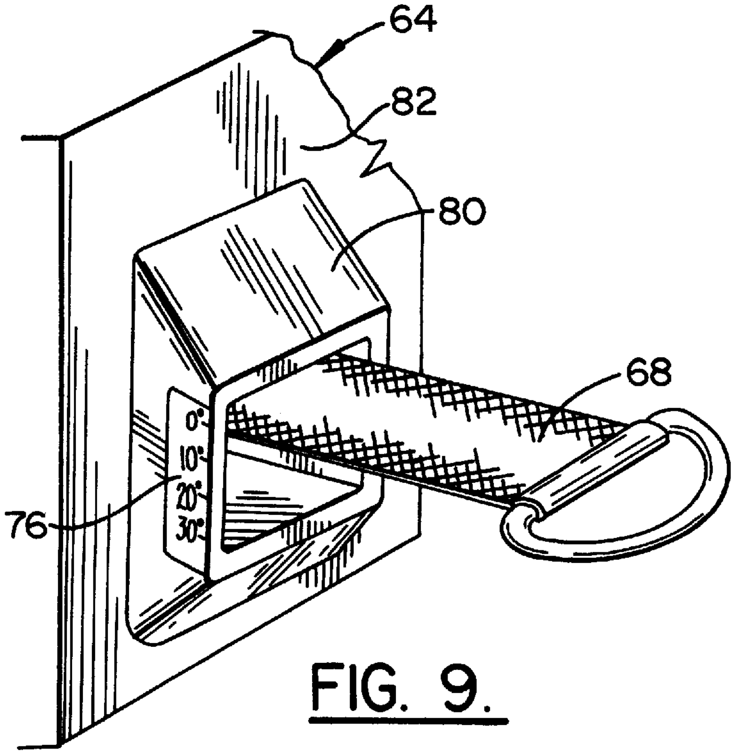
FIG. 9 is an alternate embodiment of angle indicating means useful with the present invention.

As illustrated with reference again to FIG. 8, the angle 76 is measured at the tension unit 64 as a convenient indication of angle resulting from the use of complementary angle measurements. As illustrated with reference to FIG. 9, in one embodiment of the present invention, a collar 80 is carried on a vertical surface 82 of the traction unit 64. The collar 80 receives the strap 68 therethrough for indicating the angle 76 between the strap and the vertical surface, thus indicating the angle to the axis 72 of the spine through which the pulling force 70 is exerted. Angles ranging up to 30 degrees have been shown to be effective in isolating selected areas of the lumbar spine 78, but it is not intended that their be a limitation on such a range of angles. By way of example, a 10 degree angle 76 directs the pulling force 70 of the tension unit 64 to the L5, 20 degrees for the L4, and 30 degrees for L3 in the embodiment herein described.

Figure 10:
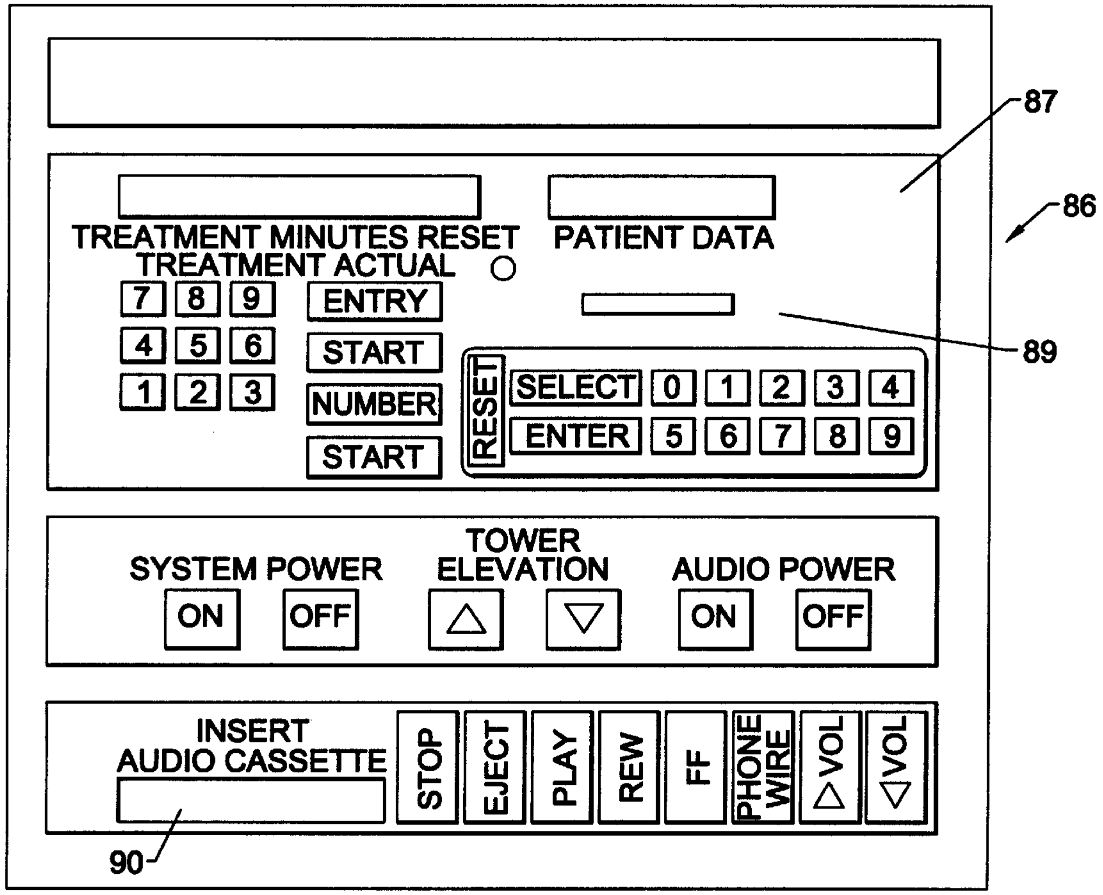
FIG. 10 is an enlarged plan view of a control panel of FIG. 1.
Figure 11:
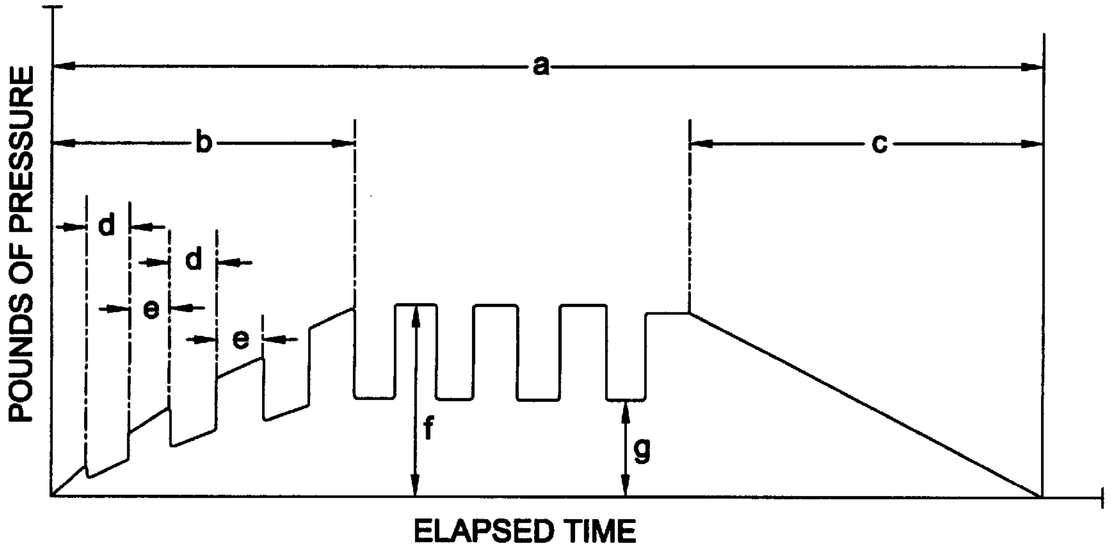
FIG. 11 is a plot of tension versus time for a programmable pre-selected treatment, by way of example.

In a preferred embodiment of the present invention, a programmable computer 84 is operable with the tension unit 64 for controlling the angle 76 and pulling force 70. A control panel 86 is carried by the support 16, as illustrated with reference agin to FIGS. 1 and 2, and to FIG. 10. A printer is carried by the frame 12 and provides a printed record at a printer output 89 positioned within the control panel 86. By way of example, and with reference to FIG. 11, control data is input through data entry buttons 87 located on the face of the control panel 86, and in a preferred embodiment include:

a. treatment time: total amount of treatment, typically from 25 to 30 minutes;

b. progressive time: time to reach treatment power from a starting point, typically about one minute;

c. regressive time: amount of time to gradually release pressure/tension from treatment, typically about one minute;

d. rest time: time between intervals, typically one half of the hold time;

e. hold time: amount of time for each interval treatment, typically one minute;

f. maximum pounds: amount of pressure/tension during hold time, typically one half of the person's body weight; and g. minimum pounds: amount of pressure during rest time, typically one half of the maximum pounds.

As illustrated again with reference to FIG. 3, by way of example, an accessory arm 88 horizontally extends above and over the table 18 from the support 16 of the frame 12. The accessory arm 88 is adapted for carrying lighting and audio components. In the embodiment, herein described, an audio cassette player 90 is carried by the control panel 86.

Figure 12:
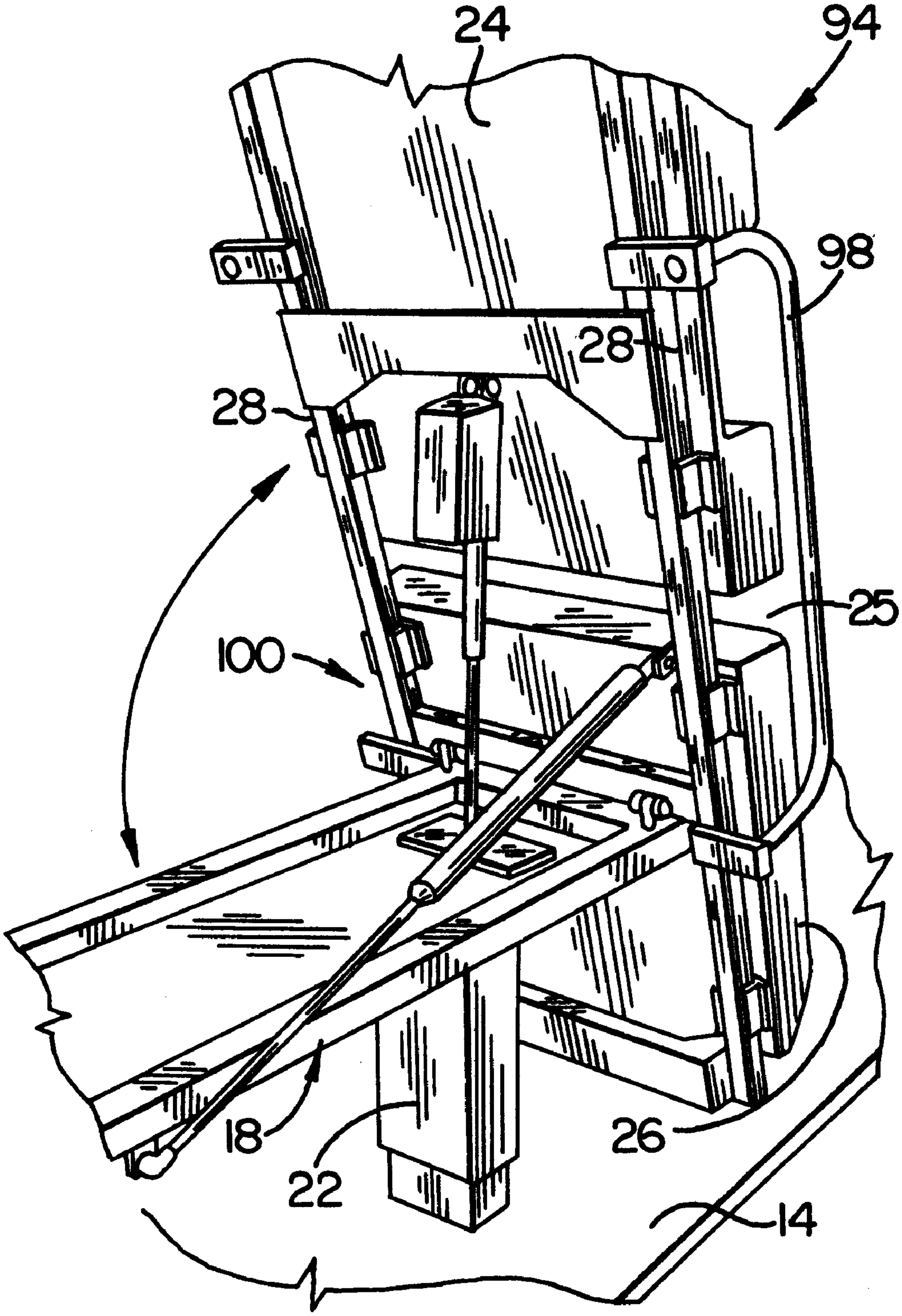
FIG. 12 is a partial rear elevation view of FIG. 4 illustrating a tilting mechanism in a preferred embodiment of the present invention.

With reference again to FIGS. 3 and 4, the table 18 is adapted for pivoting the bed 20 between a horizontal position 92 and a vertical position 94 for facilitating positioning of the person 30 onto the bed. A platform 96 is attached to an end of the lower bed portion 26 for receiving the person 30 when the bed is in the vertical position 94, see FIG. 4. The platform 96 is movable to a position distant the person when the bed 20 is in the horizontal position 92 to avoid having the pulling force 70 pull the person against the platform. In one embodiment, elongated hand rails 98 extend along the sides of the bed to provide a guide to the person during the maneuvering of the bed. As illustrated with reference to FIG. 12, a tilting mechanism 100 which can include hydraulic or pneumatic operation is used to affect table tilting. The tilting mechanism 100 works independently of the pedestal 22, thus allowing tilting and elevational movement of the table 18.

Figure 13:
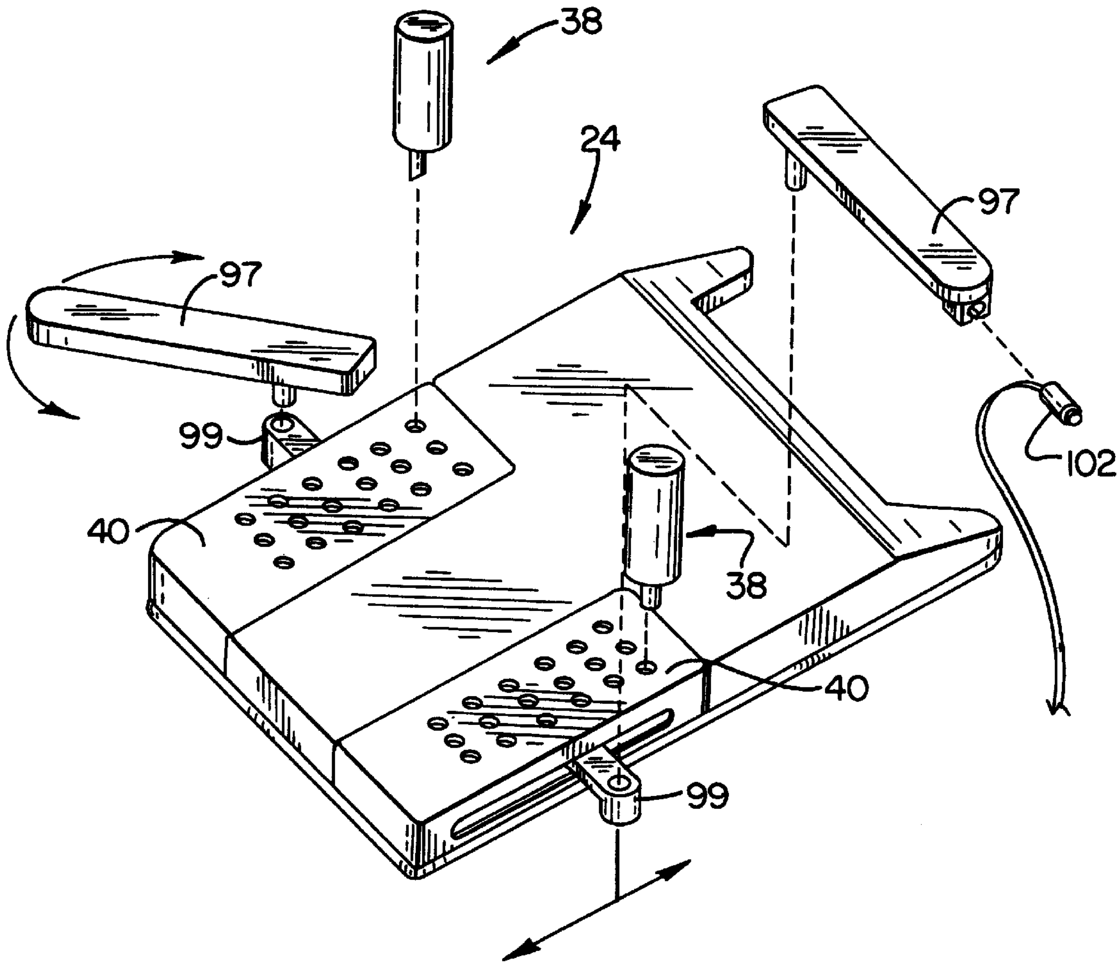
FIG. 13 is a partial exploded perspective view of a bed upper portion in an alternate embodiment of the present invention.
Figure 14:
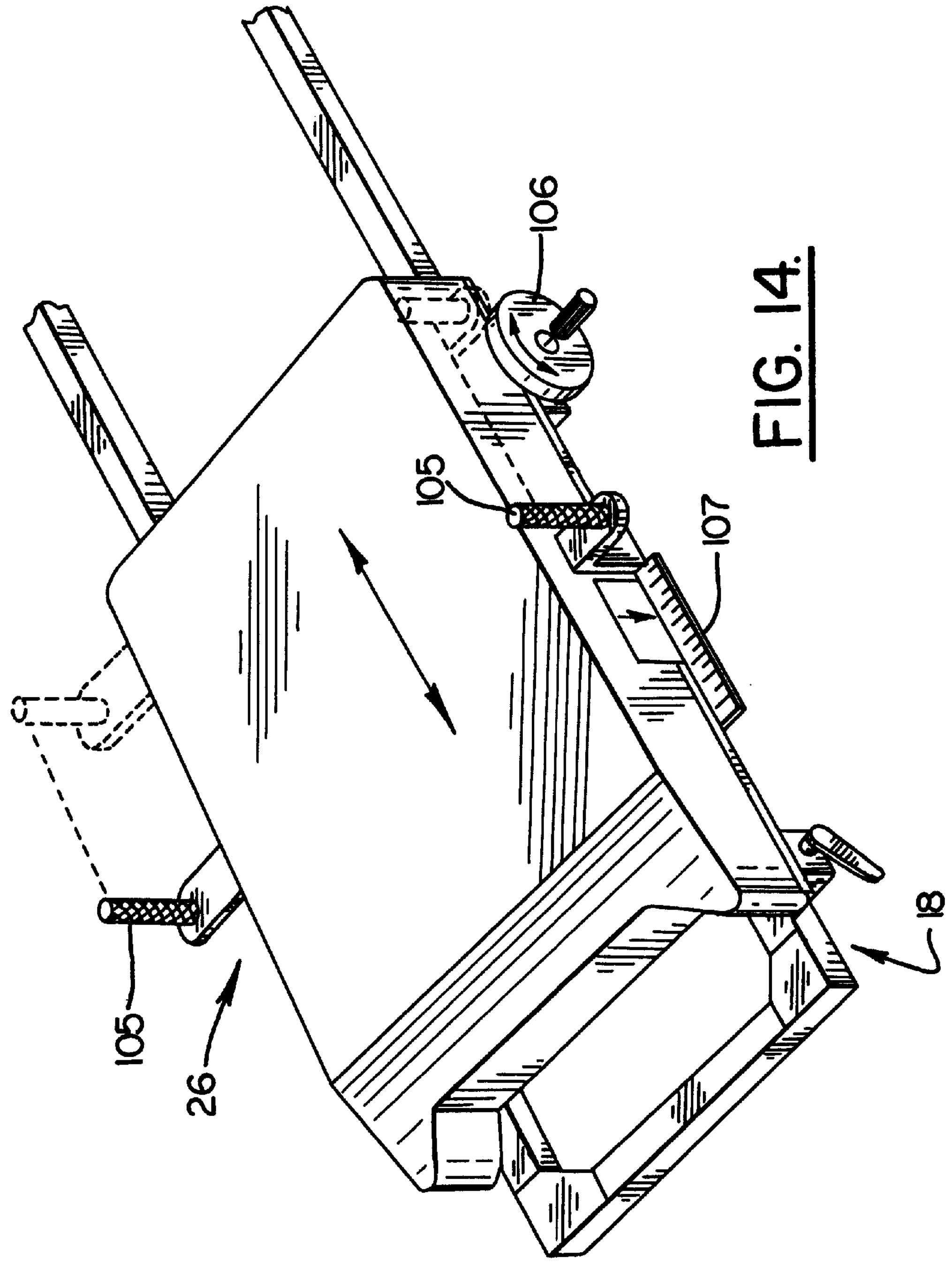
FIG. 14 is a partial perspective view of a bed lower portion in an alternate embodiment.
Figure 15:
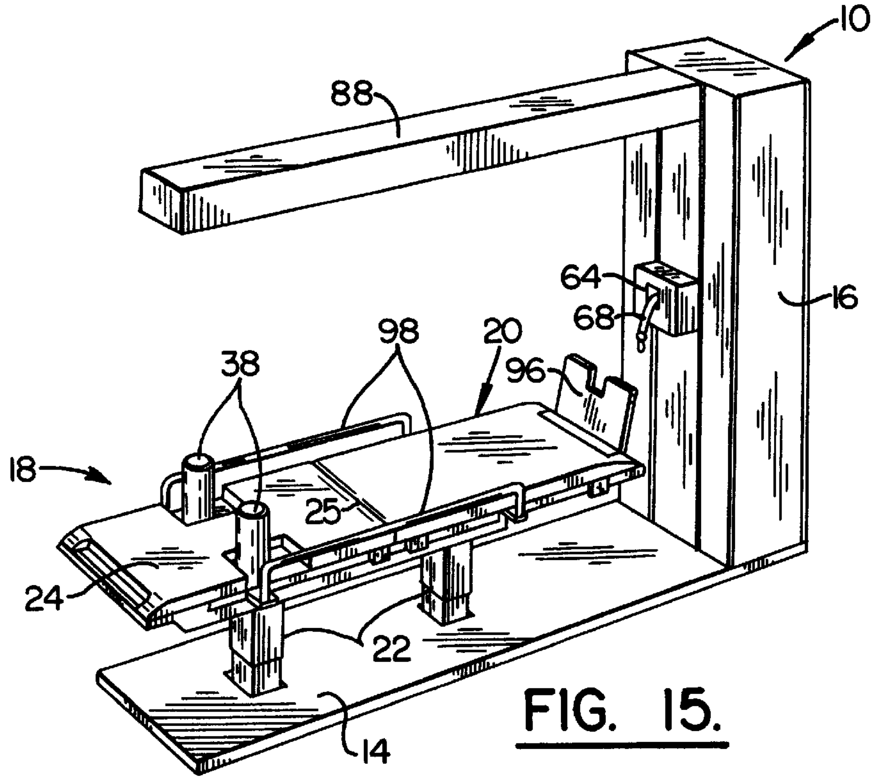
FIG. 15 is a top left, rear perspective view of the embodiment of FIG. 1.
Figure 16:
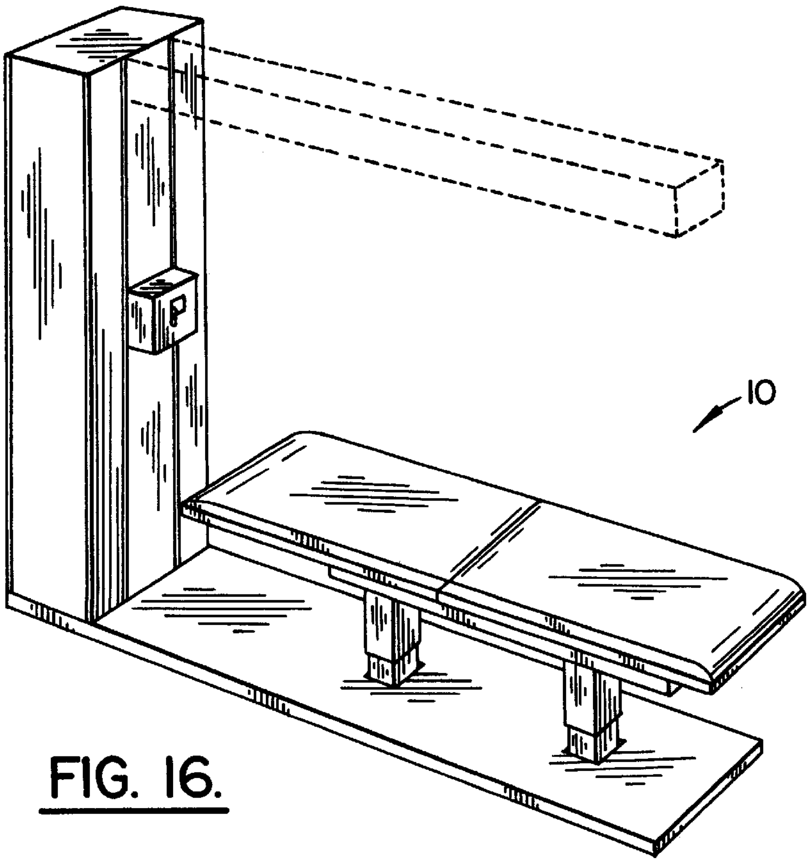
FIG. 16 is a top right and front perspective view of an alternate embodiment of FIG. 1.
Figure 17:
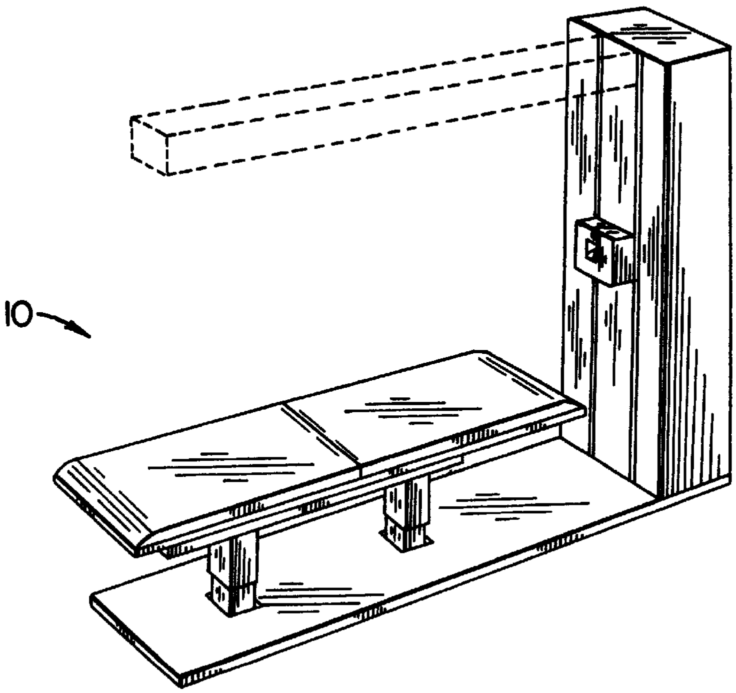
FIG. 17 is a top left and rear perspective view of FIG. 16.
Figure 18:
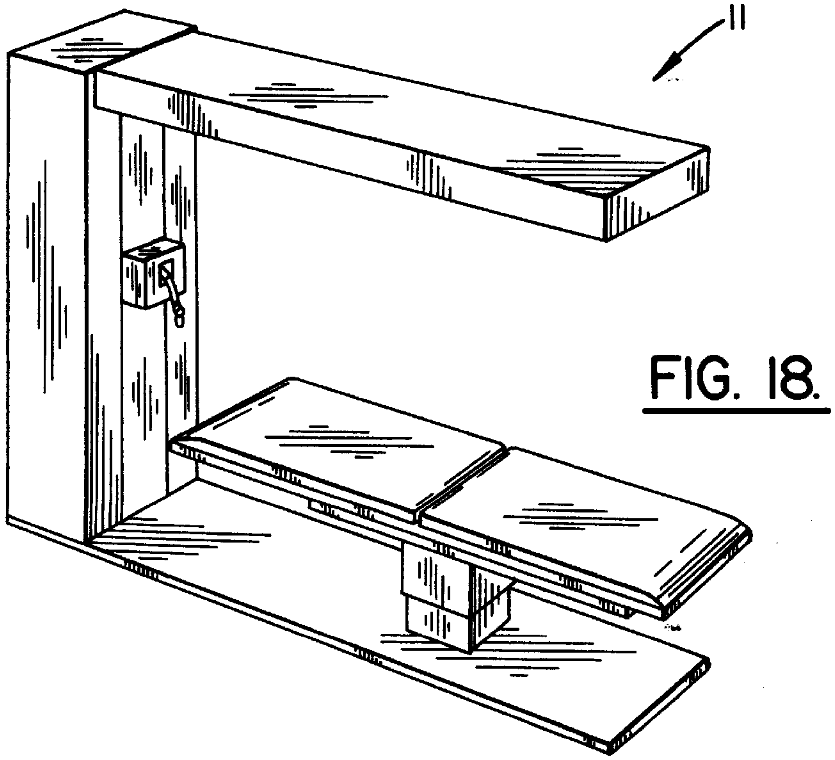
FIG. 18 is a top right, and front perspective view of an alternate embodiment of FIG. 1.
Figure 19:
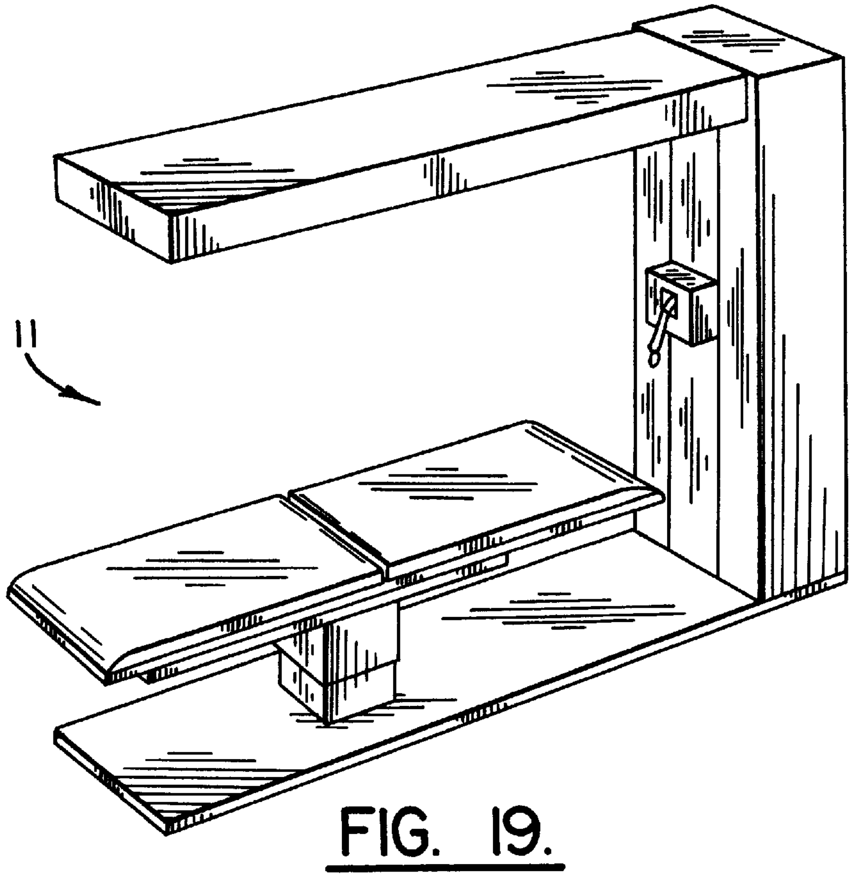
FIG. 19 is a top left, and rear perspective view of FIG. 18.
Figure 20:
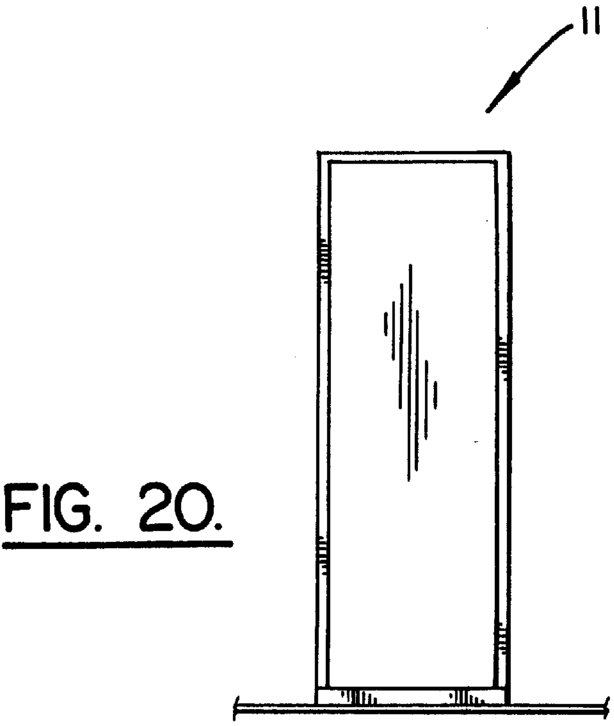
FIG. 20 is a left side elevation view of the embodiments herein described.

As illustrated with reference to FIGS. 13 and 14, an alternate embodiment of the table 18, includes the upper bed portion 24 having arm supports 38 adjustable to eighteen different arm support locations 40 on each side of the upper bed portion 24. Further, the upper portion of elongated rail 98 is replaced with rotatable arm rest supports 97 pivotable about an adjustable pivot 99. The lower bed portion 26 carries hand grips 105 movable along each side of the lower bed portion for adjustment to the person while in the vertical 92 or horizontal 94 positions of the bed. A cushion adjustment mechanism 106 and calibrated scale 107 provide for easy adjustment of the lower bed portion and grips once a setting has been established for the person.

As illustrated again with reference to FIG. 3, a safety switch 102 is operable with the traction unit 64. The safety switch 102 is accessible to the person 30 for terminating the pulling force 70 provided by the traction unit 70. A knee support 104 is movably carried on the bed 20 for providing comfort to the person 30 while in the reclined, supine position while permitting rotation of the hips of the person.

As illustrated with reference to FIGS. 15–19, the apparatus 10 takes on a unique appearance, whether as described or as illustrated in the alternate embodiment 11, and is particularly effective in providing a comfortable, non-intimidating appearance for the person 30 undergoing the treatment.

Accordingly, many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A therapeutic apparatus useful in the treatment of low back pain, the apparatus comprising:

a frame having a base and a support extending upwardly from the base;

a table having a bed and a pedestal supporting the bed above the base, the bed having an upper bed portion and an opposing lower bed portion slidable therefrom and adapted for movement while supporting a person in a supine position on the bed;

upper body anchoring means adapted for anchoring the upper body of the person to the upper bed portion;

a lower body harness adapted for attaching to the lower body pelvic portion of the person, the lower body harness having an inflatable air bladder adapted for positioning within the posterior cavity of the lumbar spine formed between the lower back of the person and the bed when the person is in the supine position on the bed, wherein the inflatable air bladder enables the local paraspinal muscles of the person to relax during a pulling force on the spine of the person;

traction means adapted for placing the persons spine in traction, the traction means carried by the upwardly extending support of the frame and attachable to the lower body harness for providing a pulling force between the upper body anchoring means and the lower body harness, the traction means vertically movable along the upwardly extending support from a position generally along a horizontal plane passing through an axis of the spine to a vertically displaced position for providing a pulling force at an angle to the horizontal plane and directing the pulling force to a preselected portion of the horizontal plane and thus adaptable for directing the pulling force to a preselected portion of the spine, wherein the traction means comprise a track carried by the upwardly extending support of the frame and a traction unit slidably carried by the track, the traction unit having a strap extending therefrom, the strap attached to the lower body harness for providing the pulling force to the harness created by the traction unit; and angle determining means operable with the traction means for indicating the angle of the pulling force to the horizontal plane and thus to the axis of the spine through which the pulling force is exerted.

2. The apparatus according to claim 1, wherein the pedestal includes pedestal sections operable for raising and lowering the bed.

3. The apparatus according to claim 1, further comprising pivotally tilting means adapted for pivoting the bed between a horizontal position and a vertical position for facilitating positioning of the person onto the bed.

4. The apparatus according to claim 3, further comprising a platform attached to the bed for receiving the person when the bed is in the vertical position, the platform movable to a position distant the person when the bed is in the horizontal position.

5. The apparatus according to claim 1, further comprising an elongated hand rail extending along a side of the bed.

6. The apparatus according to claim 1, wherein the upper body anchoring means comprise a pair of arm supports carried by the table and positionable at multiple locations for conforming to the size of the person being anchored to the bed.

7. The apparatus according to claim 6, wherein the anchoring means further comprise an upper body harness in combination with the pair of arm supports, the upper body harness having a rear strap portion for anchoring to the table and a girdle portion adaptable for extending around the upper body of the person, the girdle portion having adjustable fastening means adaptable for fitting along the chest of the person.

8. The apparatus according to claim 1, further comprising a collar carried on a vertical surface of the traction unit, the collar receiving the strap there through for indicating an angle between the strap and the vertical surface, thus indicating the angle to the horizontal plane and to the axis of the spine through which the pulling force is exerted.

9. The apparatus according to claim 1, further comprising computer controlling means operable with the traction means for controlling the angle and pulling force of the tension means.

10. The apparatus according to claim 1, further comprising an accessory arm horizontally extending from the support of the frame, the accessory arm adapted for carrying lighting and audio components.

11. The apparatus according to claim 1, further comprising a safety switch operable with the traction means, the safety switch accessible to the person for terminating the pulling force provided by the traction means.

12. The apparatus according to claim 1, further comprising a knee support movably carried on the bed and adapted for providing comfort to the person in the supine position while permitting rotation of the hips of the person.

13. A therapeutic apparatus useful in the treatment of low back pain, the apparatus comprising:

a bed having an upper bed portion and an opposing lower bed portion slidable therefrom for movement while supporting a person in a reclined position on the bed;

upper body anchoring means adapted for anchoring the upper body of the person to the bed;

a lower body harness adapted for attaching to the lower body pelvic portion of the person, the lower body harness having an inflatable air bladder for positioning within the posterior cavity of the lumbar spine formed between the lower back of the person and the bed when the person is in a supine position on the bed, the air bladder enabling the local paraspinal muscles of the person to relax during a pulling force on the spine of the person;

traction means operable with the lower body harness for providing a pulling force between the upper body and the lower body, the traction means vertically movable from a position generally along a horizontal plane passing through an axis of the spine to a vertically displaced position for providing a pulling force at an angle to the horizontal plane and directing the pulling force to a preselected portion of the horizontal plane and thus adaptable for directing the pulling force to a preselected portion of the spine, wherein the traction means comprise a frame having an upwardly extending support, a track carried thereby, and a traction unit slidably carried by the track, the traction unit having a strap attached to the lower body harness for providing the pulling force thereto; and angle determining means for indicating the angle to the axis through which the pulling force is exerted.

14. The apparatus according to claim 13, further comprising pivotally tilting means adapted for pivoting the bed between a horizontal position and a vertical position for facilitating positioning of the person onto the bed.

15. The apparatus according to claim 14, further comprising a platform attached to the bed for receiving the person when the bed is in the vertical position.

16. The apparatus according to claim 13, further comprising a elongated hand rail extending along a side of the bed.

17. The apparatus according to claim 13, wherein the upper body anchoring means comprise a pair of arm supports carried by the bed and positionable at multiple locations adapted for conforming to the size of the person being anchored to the bed.

18. The apparatus according to claim 17, wherein the anchoring means further comprise an upper body harness in combination with the pair of arm supports, the upper body harness having a rear strap portion for anchoring to the bed and a girdle portion adapted for extending around the upper body of the person, the girdle portion having adjustable fastening means for fitting along the chest of the person.

19. The apparatus according to claim 15, further comprising an accessory arm horizontally extending from the upwardly extending support, the accessory arm adapted for carrying lighting and audio components.

20. The apparatus according to claim 19, wherein the angle determining means comprise a collar carried on a vertical surface of the traction unit, the collar receiving the strap therethrough for indicating an angle between the strap and the vertical surface, thus adapted for indicating the angle to the axis of the spine through which the pulling force is exerted.

21. The apparatus according to claim 13, further comprising computer controlling means operable with the traction means for controlling the angle and pulling force of the tension means.

22. The apparatus according to claim 13, further comprising a knee support movably carried on the bed and adapted for providing comfort to the person while in the supine position while permitting rotation of the hips of the person.

23. A therapeutic apparatus useful in the treatment of low back pain, the apparatus comprising:

a bed adapted for supporting a person in a supine position wherein the spine of the person is carried within a horizontal plane;

an upper body harness adapted for anchoring an upper body portion of the person to the bed;

a lower body harness adapted for attaching to a lower body pelvic portion of the person; and traction means operable with the lower body harness for providing a pulling force between the upper body harness and the lower body harness, the traction means vertically movable from a position within a horizontal plane and thus generally along an axis of the spine, to a vertically displaced position for pulling at an angle to the horizontal plane and thus axis of the spine for directing the pulling force to a preselected portion of the spine, the traction means having angle determining means for indicating the angle to the horizontal plane and thus the angle to the axis of the spine through which the pulling force is exerted.

24. The apparatus according to claim 23, wherein the bed comprises:

an upper bed portion; and a lower bed portion slidable from the upper bed portion for movement therefrom.

25. The apparatus according to claim 23, further comprising an inflatable bladder operable with the lower body harness, the inflatable bladder adapted for positioning within the posterior cavity of the lumbar spine formed between the lower back of the person in the supine position and the bed, the inflatable bladder adapted for enabling the local paraspinal muscles of the person to relax during the pulling force on the spine of the person.

26. The apparatus according to claim 23, further comprising pivotally tilting means adapted for pivoting the bed between a horizontal position and a vertical position for facilitating positioning of the person onto the bed.

27. The apparatus according to claim 26, further comprising a platform attached to the bed for receiving the person when the bed is in the vertical position.

28. The apparatus according to claim 23, further comprising a pair of elongated hand rails extending along opposing sides of the bed.

29. The apparatus according to claim 23, further comprising a pair of arm supports carried by the bed and positionable at multiple locations and adaptable for conforming to the size of the person being anchored to the bed.

30. The apparatus according to claim 23, wherein the upper body harness comprises a rear strap for anchoring to the bed and a girdle adapted for extending around the upper body of the person, the girdle having adjustable fastening means adapted for fitting along the chest of the person.

31. The apparatus according to claim 23, wherein the traction means comprises:

a frame having an upwardly extending support;

a track carried by the upwardly extending support; and a traction unit slidably carried by the track, the traction unit having a strap extending therefrom, the strap attached to the lower body harness for providing the pulling force to the harness created by the traction unit.

32. The apparatus according to claim 31, wherein the angle determining means comprise a collar carried on a vertical surface of the traction unit, the collar receiving the strap therethrough for indicating an angle between the strap and the vertical surface, thus adapted for indicating the angle to the axis of the spine through which the pulling force is exerted.

33. The apparatus according to claim 23, further comprising an accessory arm horizontally extending above the bed, the accessory arm adapted for carrying lighting and audio components.

34. The apparatus according to claim 23, further comprising computer controlling means operable with the traction means for controlling the angle and pulling force of the tension means.

35. The apparatus according to claim 23, further comprising a knee support movably carried on the bed and adapted for providing comfort to the person in the supine position while permitting rotation of the hips of the person.

* * * * *